(12) United States Patent
Abramson

(10) Patent No.: US 7,877,273 B2
(45) Date of Patent: Jan. 25, 2011

(54) SYSTEM AND METHOD FOR EVALUATING AND PROVIDING NUTRIGENOMIC DATA, INFORMATION AND ADVICE

(76) Inventor: Fredric David Abramson, 21155 Woodfield Rd., Gaithersburg, MD (US) 20882

( * ) Notice: Subject to any disclaimer, the term of this patent is extended or adjusted under 35 U.S.C. 154(b) by 2182 days.

(21) Appl. No.: 10/338,026

(22) Filed: Jan. 8, 2003

(65) Prior Publication Data
US 2003/0158756 A1 Aug. 21, 2003

Related U.S. Application Data

(60) Provisional application No. 60/346,059, filed on Jan. 8, 2002.

(51) Int. Cl.
*A61B 5/00* (2006.01)
*G06F 19/00* (2006.01)
(52) U.S. Cl. .................... 705/3; 705/2; 600/300
(58) Field of Classification Search .............. 705/2, 705/3; 600/300; 709/224
See application file for complete search history.

(56) References Cited

U.S. PATENT DOCUMENTS

| | | | |
|---|---|---|---|
| 4,663,277 A | 5/1987 | Wang | 435/5 |
| 4,686,624 A | 8/1987 | Blum et al. | 346/20 |
| 4,796,182 A | 1/1989 | Duboff | 600/300 |
| 4,951,197 A | 8/1990 | Mellinger | 600/300 |
| 5,233,520 A * | 8/1993 | Kretsch et al. | 600/300 |
| 5,412,564 A | 5/1995 | Ecer | 600/300 |
| 5,542,420 A | 8/1996 | Goldman et al. | 600/301 |
| 5,622,861 A | 4/1997 | Kaplan et al. | 435/252.3 |
| 5,774,871 A | 6/1998 | Ferro | 705/15 |
| 5,839,901 A | 11/1998 | Karkanen | 434/127 |
| 5,937,387 A | 8/1999 | Summerell et al. | 705/2 |
| 5,954,640 A | 9/1999 | Szabo | 600/300 |
| 5,999,909 A | 12/1999 | Rakshit et al. | 705/2 |
| 6,039,989 A | 3/2000 | Bangs et al. | 426/106 |
| 6,051,385 A | 4/2000 | Fuller et al. | 435/7.1 |
| 6,083,006 A | 7/2000 | Coffman | 434/127 |
| 6,168,563 B1 * | 1/2001 | Brown | 600/301 |
| 6,196,970 B1 | 3/2001 | Brown | 600/300 |
| 6,269,339 B1 | 7/2001 | Silver | 705/2 |
| 6,306,899 B1 | 10/2001 | Cheng et al. | 514/464 |
| 6,316,203 B1 | 11/2001 | Gerald et al. | 435/7.1 |
| 6,336,136 B1 | 1/2002 | Harris | 709/219 |
| 6,358,546 B1 | 3/2002 | Bebiak et al. | 426/232 |
| 6,435,406 B1 | 8/2002 | Pentel | 235/380 |
| 6,500,621 B2 | 12/2002 | Koster | 435/6 |
| 2001/0032210 A1 | 10/2001 | Frank et al. | 707/104.1 |
| 2002/0004749 A1 | 1/2002 | Froseth et al. | 705/16 |
| 2002/0007285 A1 | 1/2002 | Rappaport | 705/2 |
| 2002/0010597 A1 * | 1/2002 | Mayer et al. | 705/2 |
| 2002/0032530 A1 | 3/2002 | Pati et al. | 702/20 |
| 2002/0032582 A1 | 3/2002 | Feeney, Jr. et al. | 705/2 |

(Continued)

*Primary Examiner*—Michelle Linh Le
(74) *Attorney, Agent, or Firm*—Konstantina M. Katcheves, Esq.; Saul Ewing LLP

(57) ABSTRACT

A method for minimizing an individual's predisposition for developing a disease including providing personal information of an individual, querying a first database of disease information with the personal information to determine a disease for which the individual has a predisposition for developing, wherein the query produces disease information, querying one or more second databases with at least a portion of the disease information and/or personal information for obtaining second information for reducing the risk for the individual developing the disease and communicating a result of the query of the lifestyle database to the individual.

22 Claims, 5 Drawing Sheets

U.S. PATENT DOCUMENTS

| | | | |
|---|---|---|---|
| 2002/0038227 A1 | 3/2002 | Fey et al. | 705/3 |
| 2002/0042725 A1* | 4/2002 | Mayaud | 705/2 |
| 2002/0047867 A1 | 4/2002 | Mault et al. | 345/810 |
| 2002/0052761 A1* | 5/2002 | Fey et al. | 705/2 |
| 2002/0111833 A1 | 8/2002 | Dick | 705/3 |
| 2002/0116227 A1 | 8/2002 | Dick | 705/3 |
| 2002/0138303 A1 | 9/2002 | Enos et al. | 705/2 |
| 2002/0142940 A1 | 10/2002 | Graham et al. | 514/1 |
| 2002/0151067 A1 | 10/2002 | Garoff et al. | 435/456 |
| 2002/0155422 A1 | 10/2002 | Ingber et al. | 435/4 |
| 2002/0155440 A1 | 10/2002 | Ljubimova et al. | 435/6 |
| 2002/0165737 A1 | 11/2002 | Mahran | 705/3 |
| 2003/0036053 A1 | 2/2003 | Maertens et al. | 435/5 |

* cited by examiner

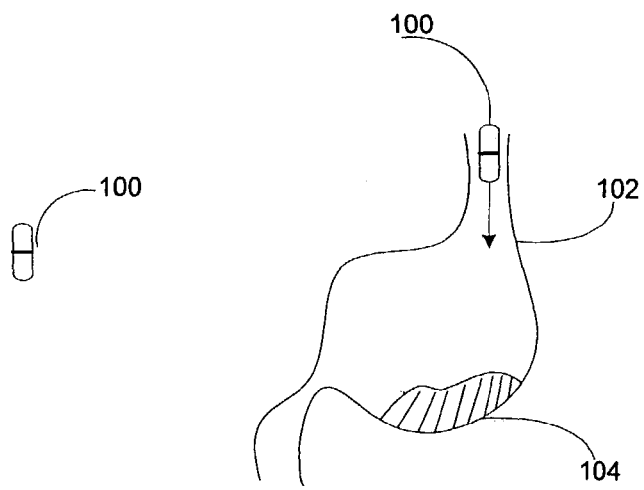
FIG 3
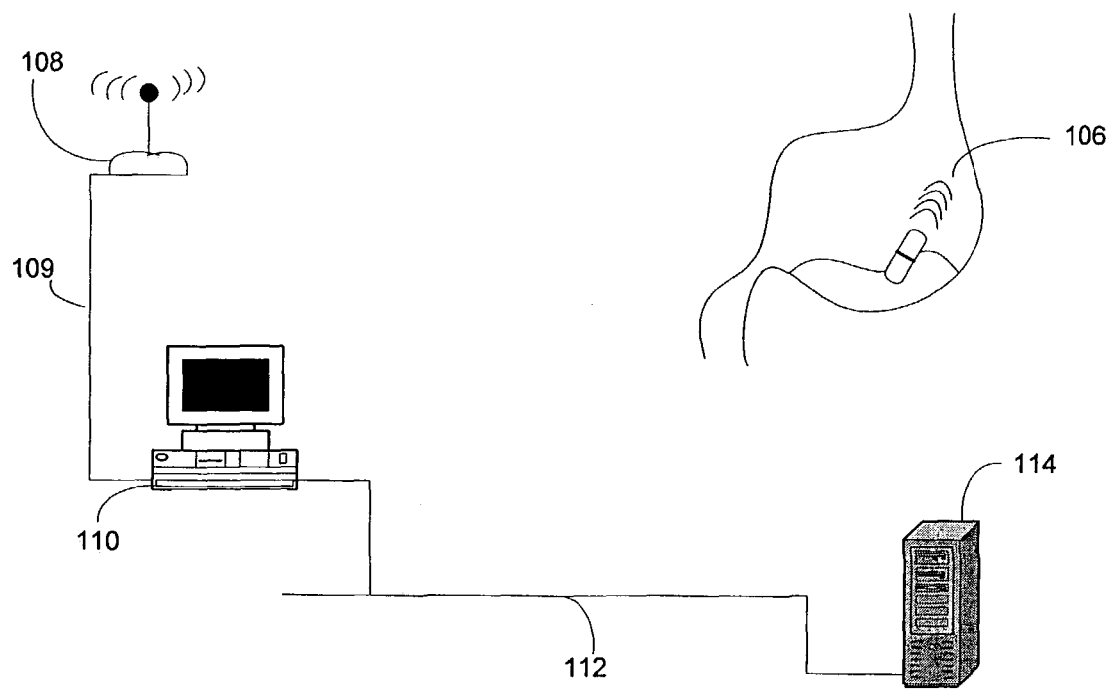
Server

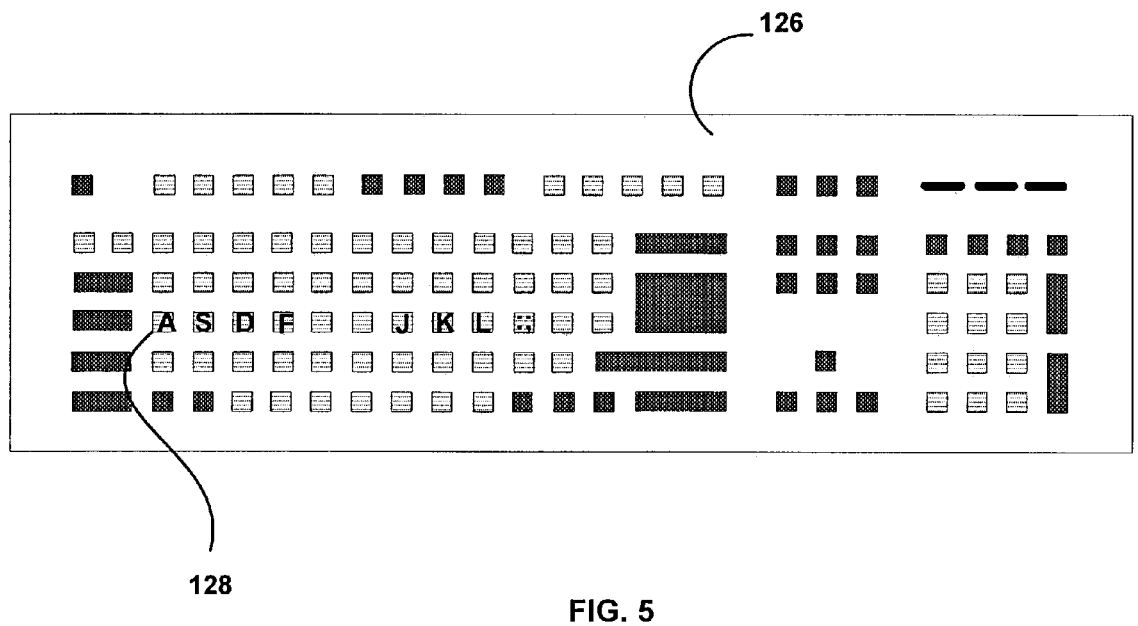
128
FIG. 5
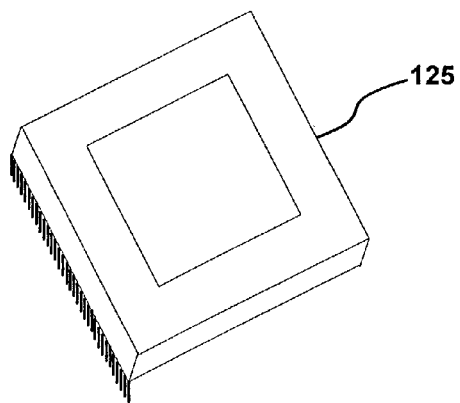

SYSTEM AND METHOD FOR EVALUATING AND PROVIDING NUTRIGENOMIC DATA, INFORMATION AND ADVICE

CLAIM TO PRIORITY

The present application claims benefit of 35 U.S.C. §119 (e) of U.S. provisional patent application No. 60/346,059, filed Jan. 8, 2002, the entire disclosure of which is herein incorporated by reference.

FIELD OF THE INVENTION

The present invention relates to nutrigenomics, and more particularly to methods and systems for evaluating an individual's genetic information and providing nutritional information and guidance, including recommendations for dietary adjustments and/or nutritional supplements, based on a predisposition of the individual for developing a particular disease or diseases based on at least one of a genetic, medical history, condition, family history, behavior, diet, and lifestyle.

BACKGROUND OF THE INVENTION

Excess weight is now considered an epidemic in America. The number and percentage of overweight Americans is growing rapidly. Worldwide, increased weight trends are observed in almost every developed country. This problem is based at least in part on poor diet/nutrition and lack of exercise.

Current diet and preventive programs are largely ineffective. The continued progression of Obesity (as well as poor diet) is a major contributing factor to a predisposition for developing chronic diseases, including heart disease and diabetes. In fact, adult type II diabetes increased by about one-third in the past ten years. This increase was greatest in the 30 to 40 year old age group. Yet, while the problems worsen, the amount of money spent on diet-related solutions continues to rise. Expenditures for dietary and nutritional problems currently exceed $100 billion annually, including $40 billion each for weight loss and diabetes. Moreover, on an individual basis, people are willing to spend substantial sums to attempt solutions. For example, the average commercial weight loss customer spends between $1,500 and $5,000 per year, often without any significant lasting benefits.

Based on the history of most preventive health programs, however, the health care system is unlikely to transform this understanding into useful information at the personal class, however. Poor diet, nutrition and lifestyle have increased, not decreased, in the past twenty years despite massive public attention and information programs by government, the health profession and academia. Accordingly, these problems have translated into a alarming increase in obesity in America in the past ten years and an unprecedented rise in lifestyle and nutrition related diseases.

Although there exists a number of new and convention methods for good health, diet and nutrition, they simply are not working. Experts have advised the Federal Trade Commission that only one in twenty people are able to lose weight and keep it off with current diet/exercise plans.

The failure of these diet models is due to one or more problems. For example, many programs require people to travel to a facility at inconvenient times (e.g., during normal business hours and shortly thereafter). Almost all programs provide too much information which is hard to digest, remember and use. People are often left on their own to work out a course of action. Little attention is often paid to a person's individual problems and/or needs. Furthermore, many diet plans are too complicated for sustained use.

Another major health trend facing the developed world is the ability to determine an individual's predisposition for developing a disease based on the individual's genetic makeup. The advances in genomics mean it will soon be possible to screen people for defective genes before the manifestation of the defect becomes apparent. Moreover, unraveling of the human genome will also vastly improve knowledge of molecular and biochemical processes. Such knowledge will thus provide a better understanding of how diet/nutrients affect our health and well being.

Compelling links are known to exist between genetics, nutrition, and disease. Nutritional imbalance is associated with a variety of chronic diseases, including cancer, heart disease, arthritis, obesity, asthma, allergy, and lower immunities. Adjusting diets and ingesting certain nutrients and dietary supplements are known to lower the risks of many conditions, including heart disease, osteoporosis and some cancers.

Accordingly, there is a need to develop systems and method for creating and implementing health, well-being and diet/nutrition plans that will help prevent diseases. These and other drawbacks exist.

SUMMARY OF THE PRESENT INVENTION

One aspect of the invention is directed to a system and method which combines dietary supplements with quick access to live counselors and personal guidance. Embodiments of the present invention break information into tiny chunks that an individual can understand and use, at the time when and place where the individual needs the information. Personalized advice may be built around each individual, based on various factors including the individual's genetic make-up. In addition, the present invention may communicates scientific and medical information and provide personalized advice for eating and supplementing the individual's diet.

In the present invention, an individual's genetic risk profile is synchronized and linked with an optimized profile of micronutrients and other food constituents. Individualized action plans that focus on lifestyle and dietary intervention are then formulated with an aim toward, for example, preventing or delaying the onset of disease. Specifically, the present invention makes use of large-scale databases containing scientific information regarding nutrition, micronutrients, other dietary elements, coupled with information collected from clients and other sources. The data may also include demographic and economic information, eating patterns and food purchases in restaurants and grocery stores. Additional databases may also be used including nutritional content information, genomics and proteomics, and databases describing interactions between and among foods, medications, dietary supplements. Also, medical information of the individual may also be included.

For example, an individual wanting to lower the risk of heart disease will receive a complete program that includes dietary adjustments and supplements, live counselors, food planning, and other information about reducing the risk of heart disease. This may include weight loss, cholesterol reduction and other relevant information.

In a first aspect of the present invention, a method for minimizing an individual's predisposition for developing a disease includes providing personal information of an individual, querying a first database of disease information with the personal information to determine a disease for which the individual has a predisposition for developing, wherein the query produces disease information, querying one or more second databases with at least a portion of the disease information for obtaining second information for reducing the risk for the individual developing the disease and communicating a result of the query of the second database to the individual.

In another aspect of the present invention, a method for minimizing the risk of an individual in developing a disease for which the individual has a predisposition of developing includes providing first information of an individual's predisposition for developing a disease, querying one or more second databases with at least a portion of the first information, wherein a result of the query produces second information for reducing the risk for the individual developing the disease and communicating the result to the individual.

In another aspect of the present invention, a system for minimizing an individual's predisposition for developing a disease includes first querying means for querying a first database of disease information with personal information of an individual to determine a disease for which the individual may have a predisposition for developing, wherein the query produces disease information, second querying means for querying one or more second databases with at least a portion of the disease information for obtaining a second information for reducing the risk for the individual developing the disease and communicating means for communicating the second information to the individual.

In another aspect of the present invention, a system for minimizing the risk of an individual in developing a disease for which the individual has a predisposition of developing includes providing means for providing first information of an individual's predisposition for developing a disease, querying means for querying one or more second databases with at least a portion of the first information, where a result of the query produces second information for reducing the risk for the individual developing the disease, and communicating means for communicating the second information to the individual.

In yet another aspect of the present invention, a method for determining whether consumption of an item falls within a lifestyle for minimizing an individual's predisposition for developing a disease includes inputting a code of a product for consumption by an individual into a wireless communication device, communicating the code via the wireless communications device to a remote system, receiving the code by the remote system, determining the product associated with the code, querying a first database of lifestyle information to determine whether the product or a closely related product is contained therein and communicating the determination from the remote system to the wireless communication device.

In another aspect of the present invention, a system for determining whether consumption of an item falls within a lifestyle for minimizing an individual's predisposition for developing a disease comprises inputting means for inputting a code of a product for consumption by an individual into a wireless communication device, first communicating means for communicating the code via the wireless communications device to a remote system, receiving means for receiving the code by the remote system, determining means for determining the product associated with the code, querying means for querying a first database of lifestyle information to determine whether the product or a closely related product is contained therein and second communicating means for communicating the determination from the remote system to the wireless communication device.

In another aspect of the present invention, a method for determining whether consumption of an item falls within a lifestyle for minimizing an individual's predisposition for developing a disease, the method includes inputting a code of a product for consumption by an individual into a wireless communication device, communicating the code via the wireless communications device to a remote system, receiving the code by the remote system, determining the product associated with the code, determining the associated nutritional profile of the product, querying a first database of lifestyle information to determine whether the nutritional provide of the product fall within a lifestyle of the individual and communicating the determination from the remote system to the wireless communication device.

In another aspect of the present invention, a system for determining whether consumption of an item falls within a lifestyle for minimizing an individual's predisposition for developing a disease includes inputting means for inputting a code of a product for consumption by an individual into a wireless communication device, first communicating means for communicating the code via the wireless communications device to a remote system, receiving means for receiving the code by the remote system, first determining means for determining the product associated with the code, second determining the associated nutritional profile of the product, querying means for querying a first database of lifestyle information to determine whether the nutritional provide of the product fall within a lifestyle of the individual and second communicating means for communicating the determination from the remote system to the wireless communication device.

In another aspect of the present invention, a method for determining whether an item falls within a lifestyle for minimizing an individual's predisposition for developing a disease includes providing an electronic identification on the lifestyle item, communicating the electronic identification via a wireless communication device to a remote system, determining the lifestyle item associated with the electronic information, querying a first database of lifestyle information to determine whether the lifestyle item is associated with data contained therein, forwarding the determination from the remote system to the wireless communication device and presenting the determination with the wireless communication device.

In another aspect of the present invention, a system for determining whether an item falls within a lifestyle for minimizing an individual's predisposition for developing a disease includes an electronic identifier provided on the lifestyle item, communicating means for communicating the information contained in the electronic identifier via a wireless communication device to a remote system, determining means for determining the lifestyle item associated with the electronic information, querying means for querying a first database of lifestyle information to determine whether the lifestyle item is associated with data contained therein and forwarding means for forwarding the determination from the remote system to the wireless communication device, presenting means for presenting the determination with the wireless communication device.

In another aspect of the present invention, a method for producing a customized supplement for an individual for minimizing an individual's predisposition for developing a disease and/or maintaining health includes providing personal information of an individual, querying a first database of disease information with the personal information to determine a disease for which the individual has a predisposition for developing, where the query produces disease information regarding the individual's predisposition for developing a disease, and querying a supplement database with at least a portion of the disease information and/or a portion of the personal information to determine one or more dietary supplements to be ingested by the individual to minimize the individual's predisposition for developing the disease and/or maintaining health.

In yet another aspect of the present invention, a system for determining whether a medication has been ingested by an individual includes a radio transmitter in the shape of a capsule for oral administration to an individual along with a medication and a radio receiver. Upon the capsule being orally administered to the individual, a bodily fluid in contact with the capsule causes the radio transmitter to transmit a radio signal to the radio receiver.

In another aspect of the present invention, a method for tracking the oral administration of a medication by an individual includes providing a radio transmitter in the form of a capsule for administering orally to the individual along with a medication, providing a radio receiver for receiving radio signals generated by the radio transmitter, providing a computer system in communication with the radio receiving for logging a time at which a radio signal is received, orally administering the radio transmitter capsule to the individual, transmitting a radio signal by the radio transmitter upon the capsule being exposed to a bodily fluid, receiving the radio signal by the radio receiver, communicating a second signal to the computer and logging a time at which the second signal is received by the computer.

In still yet another aspect of the present invention, a system for determining whether a medication has been ingested by an individual includes a radio transmitter provided in a package of medication for administering to an individual and a radio receiver, wherein upon the package being opened, the radio transmitter transmits a radio signal to the radio receiver.

In another aspect of the present invention, a method for tracking the oral administration of a medication by an individual includes providing a radio transmitter in a package of medication, providing a radio receiver for receiving radio signals generated by the radio transmitter, providing a computer system in communication with the radio receiving for logging a time at which a radio signal is received, opening the package to obtain the medication for the individual, transmitting a radio signal by the radio transmitter upon the package being opened, receiving the radio signal by the radio receiver, communicating a second signal to the computer and logging a time at which the second signal is received by the computer.

In another aspect of the present invention, a keyboard for use with a computer system comprising a plurality of keys for inputting information and at least one biometric sensor positioned on at least one of the keys.

Still other embodiments of the present invention are directed to computer readable mediums having computer instructions provided thereon for enabling a computer to perform one or more of the method embodiments outlined above. Other embodiments also include application programs for a computer system which enable the computer to perform any one or more of the method embodiments recited above.

It will be appreciated by one of ordinary skill in the art that generally, substantially all of the means outlined above for any of the system aspects of the present invention, may be accomplished via computer hardware and corresponding software processes of a computer system(s).

These and other advantages, objects and features of the invention will be apparent through the detailed description of the embodiments and the drawings attached hereto. It is also to be understood that both the foregoing general description and the following detailed description are exemplary and not restrictive of the scope of the invention.

BRIEF DESCRIPTION OF THE DRAWINGS

FIG. 3 illustrates a tracking system according to an embodiment of the present invention.

FIG. 5 illustrates a biometric keyboard according to another embodiment of the present invention.

DETAILED DESCRIPTION OF THE PREFERRED EMBODIMENTS

Figure 1:
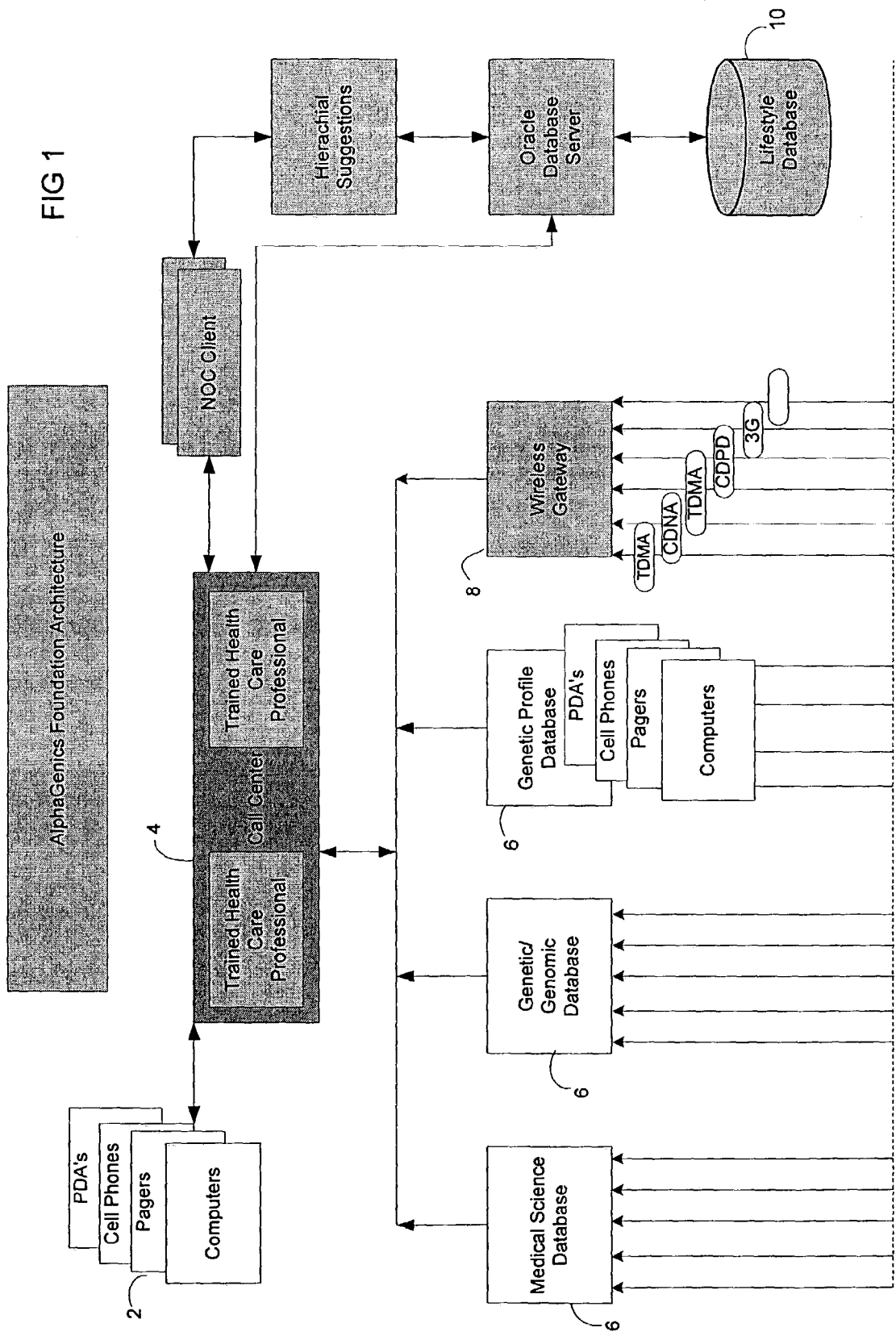
FIG. 1 illustrates an overview of a system architecture according to some embodiments of the present invention.

Embodiments of the present invention relate to methods and systems for minimizing or reducing an individual's predisposition for developing a disease including providing personal information of an individual including genetic, lifestyle, medical, physical, demographic, and/or other information, querying a first database of disease information with the personal information to determine a disease for which the individual has a predisposition for developing, wherein the query produces disease information, querying a lifestyle database with at least a portion of the disease information for obtaining a lifestyle item for reducing the risk for the individual developing the disease and communicating a result of the query of the lifestyle database to the individual.

Accordingly, in addressing the predisposition of individuals to develop diseases, medical conditions and the like, individuals may be broken down into one or more predetermined classes based on various criteria. These criteria may relate to genetic conditions related to disease, family history of disease, manifestations of disease, physical or health conditions which may relate to or lead to disease, other biological or non-biological demographic factors and/or other criteria. For example, according to one embodiment, individuals may be classified generally into one or more of five (5) different classes:

Class 1. Individuals in this class have one or more genes known to be linked to specific disease(s). Examples include the BRAC-I gene for cancer or the gene for Huntington's Disease. The risk of the disease appearing in people in this class is directly related to how the defective genes are controlled. Defective genes may be controlled, for example, by specific combinations of various nutrients, bioactive chemicals in foods, dietary supplements, etc.

Class 2. Individuals in this class are aware of their genetic risk because of information about their family. For example, a thirty year old female whose sister, mother and both grandmothers had breast cancer before age 50 is at substantially greater risk of breast cancer than another 30 year old with no family history of breast cancer. Similar risk factors are known for many other diseases. In this class, though the existence of a specific set of genes is not verified, the elevated risk indicated by family history justifies, for example, implementing a healthy eating strategy that will lower the risks should the genes be present.

Class 3. Individuals are classified here when the appearance of a specific disease highlights an increased risk of later developing another disease. For example, having Type II diabetes increases the risk of later heart disease. High blood pressure is linked to an increased risk of heart attack. Proper combinations of food, supplements and medication, for example, can both decrease the severity of the disease requiring treatment and simultaneously, lower the chance of later developing one of the follow-on diseases.

Class 4. Individuals in this class have some general health condition which, by itself~ presents little risk but which is known to be correlated with increased risks of developing a major health problem. Examples here include excess weight (as a precursor to type II diabetes) and high cholesterol (as a precursor to heart attacks).

Class 5. Individuals in this class have no health conditions that indicate specific risk factors. They are generally healthy. However, even in healthy populations, demographic subgroups are known to carry increased risks. Examples of biologic demographic factors are age and gender. Non-biologic factors such as education and occupation are also known pointers for differential risk.

Disease Risk-Prevention Model

Let the probability that an individual in Class 5 will develop a specific genetic disease be $P_D(5)$. Similarly, let the respective probabilities that individuals in Class 4, Class 3, Class 2 and Class 1 develop specific genetic diseases be $P_D(4)$, $P_D(3)$, $P_D(2)$, and $P_D(1)$, respectively. In some embodiments of the invention and for purposes of this discussion, the probability that a particular individual will develop a specific genetic disease is lowest at Class 5, and increases until it is highest at Class 1. Thus, $P_D(5) < P_D(4) < P_D(3) < P_D(2) < P_D(1)$.

Once the risk of getting a specific disease is identified, based on the individual's classification, the probability of preventing the disease through some sort of intervention may be estimated. For purposes of illustration and not by way of limitation, two different outcomes are lumped together:

Outcome I: postponement of the date of onset of the disease; and

Outcome II: reduction of the severity of the disease once it is expressed.

Other outcomes and/or number of outcomes may be used as would be apparent.

In some cases, both of the given outcomes may occur. That is, for some diseases, the date of disease onset may be postponed, and then when the disease is expressed, its severity is reduced. Thus, if $P_P(i)$ corresponds to the probability of preventing or postponing a specific disease for an individual in for the i-th class, then $P_P(5) < P_P(4) < P_P(3) < P_P(2) < P_P(1)$.

This of course assumes that the more specificity in the knowledge of an individual's risk, the better able that preventative steps may be taken.

Third is the estimate of the desire of people to seek help at each class. An assumption is made that the desire to seek help is related to the amount of specificity in determining an individual's future risk. In other words, an individual in Class 5 is less likely to seek help to prevent a specific disease than an individual in Class 4. Similarly, individuals in Class 3 will be more motivated than one in Class 4, etc.

Thus, if $P_C(i)$ corresponds to the probability (desire) of seeking an intervention for the i-th class, then $P_C(5) < P_C(4) < P_C(3) < P_C(2) < P_C(1)$.

Given the above, the probability of an individual in any class being a candidate for the methods and systems for the present invention may be estimated. Thus, P(i) for the i'th Class may be expressed as:

$P(i) = P_D(i) \cdot P_P(i) \cdot P_C(i)$.

In other words, the probability that an individual is a candidate is the product of the chances of getting the disease without any preventive action, the chances of preventing the disease by taking one or more actions, and the desire to take action to try to prevent the disease.

The chances of getting the disease may be measured both objectively (an epidemiological/statistical/biochemical assessment) and subjectively (an individual's perception of the chances of getting the disease). For purposes of these discussions, these two measures will be initially considered to be the same, though it is known that they typically differ. The key is that unless an individual actually perceives a risk of actual disease, no action is possible regardless of what medical or scientific information there is.

Database Domain Descriptions

Databases for use in the present invention generally include four main data domains: scientific knowledge, genetics, lifestyle, and transactional. Using artificial intelligence and data mining processes, the most appropriate data associated with an individual's unique problems and that assists in developing individualized solutions for diet, lifestyle and/or behavioral changes may be obtained from each data domain. These data domains facilitate research regarding which supplements work best in which situations, what side effects and problems are being experienced, and other feedback. This feedback allows for continual improvement of the individual's diet/lifestyle. Accordingly, the following are brief descriptions of the databases used in the present invention.

Scientific: the scientific data domain includes knowledge about various areas that relate to nutrition and nutritional problems. These may include, for example, nutrients, foods, nutrition, human behavior, medicines, biochemistry, physiology, and diseases.

Genetic: the genetic data domain includes, for example, the knowledge of the human genome, how genes are expressed functionally in proteins and other biochemical, physiologic, and neurological actions, etc. This domain may also include genetic information obtained from individuals as a result of genetic testing.

Lifestyle: the lifestyle domain includes data obtained about each individual's lifestyle, behavior, and habits. This data may include, for example, the basic socioeconomic, demographic, and/or health data as well as what foods are eaten and when, eating habits, and daily living information (e.g., whether an individual drives to work or uses public transportation can be important in understanding their dietary options). The data included within this domain is dependant upon the amount and nature of contact with each individual.

Transactional: the transactional domain includes details about interactions between various aspects of the invention and individuals using them. This data may include, for example, recordings of all telephone counseling sessions, copies of screens accessed by counselors in a session, data about calls including times and length, and sales, etc.

The present invention may also make use of existing databases. For example, these existing databases include disease databases such as, for example, the CDC (http://www.cdc.gov/), Medscape (http://www.medscape.com/), the National Library of Medicine (http://www.ncbi.nlm.nih.gov/pubmed/), Bionet (http://www.bio.net/), the human genome (http://www.hgmp.mrc.ac.uk/Genome Web/), etc.

FIG. 1 illustrates an exemplary system that may be used to implement various aspects of the invention. Accordingly, the invention may be directed toward an individual (male or female), who has been genetically tested and diagnosed with a predisposition for possibly developing a particular disease (e.g., cancer or diabetes), and who seeks information on controlling the disease through lifestyle changes. Such lifestyle changes may include, for example, diet/nutritional, personal habits, exercise, profession, etc. Nutrition and dietary changes are generally the key elements of information provided via this embodiment, but any lifestyle factor may be relayed to the individual seeking information on preventing the disease.

Thereafter, in some embodiments, an individual may initiate an inquiry through a communications device 2, which may include a wired device (i.e., telephone, internet, facsimile, etc.) or wireless device (i.e., cellular telephone, PDA, etc.) to a remote system that performs one or more aspects of the present invention. In some embodiments, the inquiry may be initially received by a trained health professional in a call center 4 who interacts with a front-end application processor (for example) to address the inquiry made by the individual. The front-end application processor generally includes quantitative tools to sift and prioritize the problem and potential solution sets to be relayed to the individual. The health professional (or a software) uses this information to produce a query.

Queries may be subsequently routed through a series of processes in which various data management rules and analysis routines may be applied to the query, using a set of back-end processors (for example) attached to a number of different knowledge databases 6. Such knowledge databases may include, for example, physiology information, medical science information, nutrient information, genetic information, algorithms for associating disease development with risk factors, genetic profile information of the individual, etc. These knowledge databases and/or other data may also be accessed using various mechanisms including wireless gateways 8 as would be apparent.

In instances where the individual has not yet been diagnosed with a predisposition for developing a disease, queries may also be directed toward a disease database to determine if the individual has a predisposition for developing one or more diseases.

The results of these queries produce information relating to lifestyle suggestions for the individual to minimize the individual's predisposition for developing the one or more diseases. These results may be communicated to the individual via, for example, any one or more ways using fax, wireless devices, email, postal mail, etc.

The results of the queries together with the personal information captured about the individual (e.g., age, genetic makeup, height, weight, etc.) as well as eating habits and lifestyle actions are used to populate a personalized lifestyle database 10, which may house general and specific suggestions for nutrition, dietary, and behavior changes. The lifestyle database continues populating itself as the individual continues to contact and/or interact with the system, based on their curiosity and/or quest for specific information (such as "can I have broccoli today" instead of "is there something bad I should not eat today"). Moreover, ultimate tasks that embodiments of the present invention accomplish include linking the lifestyle database with the other databases to identify context-specific behavioral suggestions. In addition, as the lifestyle database becomes populated, hierarchical suggestions may be made to the individual.

Once the query is satisfied, the trained health professional may respond in real-time to the individual through various mechanisms including, for example, cellular phones, personal-digital-assistants, the Internet, etc., using either voice or other data streams (e.g., text, video, images, pre-recorded audio, multimedia, etc.). In some embodiments, emerging technologies may eliminate the need for the intermediate health care professional. In other embodiments, the intermediate health care professional may facilitate the use of the invention by providing a detailed understanding of human behavior.

Information about the individual's personal preferences and lifestyle may be analyzed so that suggestions are both practical and acceptable. For example, steak dinners should not be suggested to a vegetarian, or broccoli to someone who prefers carrots. Information about a food's nutritional value and composition that allows prevention of nutrition-related disease or other heath problems may also be analyzed. In addition, for those customers taking medications, integration of the analysis with information about side effects and contraindications of the medication, may help the individual avoid things that may interact with that medication. These and other aspects of the invention eliminate the difficult burden, for example, of having to remember vast quantities of information about food and eating, thereby making it easier to do the right things at the right time.

Figure 2:
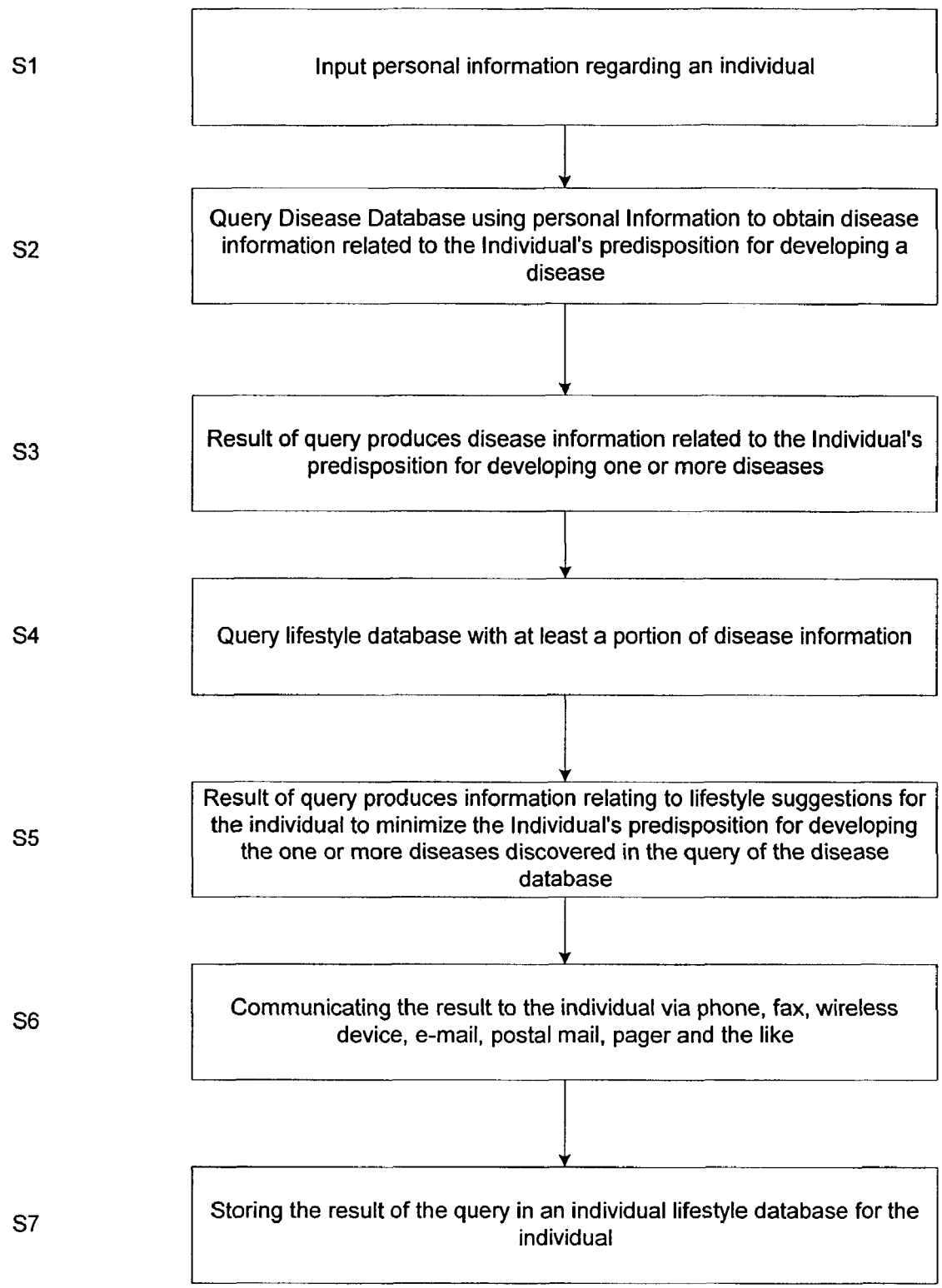
FIG. 2 illustrates an overview of a process flow according to an embodiment of the present invention.

FIG. 2 illustrates an operation of one embodiment of the invention. In an operation S1, an individual's personal information is gathered and input into call center 4, as discussed above. This personal information may include any of genetic information, lifestyle information, medical information, physical information, demographic information, and/or other information that may be related to, or useful for assessing, the individual's health. In an operation S2, at least a portion of the personal information may be used to formulate a query to a disease database to obtain disease information related to the individual's predisposition toward a disease (or disease as would be apparent). In an operation S3, the disease information is received.

In an operation S4, at least a portion of the disease information may be used to formulate one or more queries to various databases that include information regarding findings, recommendations, suggestions, guidelines, treatment, indications and/or contraindications etc., related to the disease, and more particularly lifestyle suggestions associated with delaying the onset of or reducing the deleterious effects of the disease. As discussed herein, in some embodiments of the invention, the lifestyle suggestions may include dietary, nutritional, and/or behavioral recommendations. As would be appreciated, this operation may include one or more intermediate queries among these or other databases in order to finally identify specific lifestyle suggestions associated with the particular disease. In an operation S5, the lifestyle suggestions are produced. In some embodiments of the invention, the lifestyle suggestions may be compared with personal information to tailor them to the individual.

In an operation S6, the lifestyle suggestions may be communicated to the individual using one or more communications channels as discussed herein. In an operation S7, the lifestyle suggestions are stored in an individual lifestyle database.

According to some embodiments of the invention, multiple communication channels may be provided to accommodate various individual preferences, availability, access, etc. The integration of these multiple communication channels ensures precise and accurate information may be delivered to the individual at any time and any place. This makes it easier for individuals to make adjustments without bearing the burden of becoming a food expert. Some embodiments of the invention may also be used in times when a consumer needs to keep from eating/taking something that will aggravate, or help to develop a condition (e.g., auto dial to the system so that one may talk to a health professional to stop from buying a package of cigarettes, for example).

In some embodiments, various information, in various quantities, may be provided to the individual at any desired time. This information may be regarding the individual's food choices. For example, the system may assist the individual by evaluating what is in a food, recommending a food choice(s) at the point of sale or ingestion, identifying complementary foods, or helping in the adjustment to different food quantities. This approach facilitates small, incremental lifestyle and eating adjustments for the individual that ultimately provides long term and sustained health benefits.

In one embodiment of the present invention, an individual who desires to determine whether a particular food stuff may be consumed, may scan a bar code with, for example, a portable wireless device having a bar code scanner integral thereto, or connected therewith (e.g., cell phone, PDA, pager in communication with a bar code reader/scanner). These bar codes may correspond to a UPC code of a particular food stuff at a grocery store, a code on a menu at an affiliated restaurant or similar establishment, or other encoding mechanism operable with a scanner for identifying the food stuff. For example, when the individual is shopping for groceries, the individual may scan various products using the bar code scanner and communicate this information to the system via the wireless device. In some embodiments, this information may be forwarded to the call center, where the individual's personal lifestyle database is located. This process may be handled through the trained health professional, or may be automated.

The scanned product(s) may then be determined, and based on the individual's personal lifestyle database, a recommendation as to whether the product(s) may be purchased and/or consumed by the individual is provided. If the product is not in the individual's lifestyle database, then, upon the call center receiving the bar code, the system may identify the product corresponding to the bar code. Then, using the appropriate queries applied to various databases, the system determines whether purchasing and/or consuming the product is advisable. This information may be then, in turn, stored for future reference in the individual's lifestyle database.

Medication/Supplement Prompting

The present invention also includes methods and systems for helping customers keep track of medications and supplements they need to take. Accordingly, timely reminders to at least one of cell phones, pages and/or email may be sent to alert an individual to take a supplement, a food, and/or a medication. This communication provides the added opportunity to include other marketing messages and general information. Moreover, reminders may be downloaded to an individual's PDA, scheduling or calendaring program on the individual's computer, etc.

Individualized Supplement Formulations

In this embodiment, individually formulated supplement combinations may be produced based on an individual's genetic, metabolic and/or lifestyle profile to minimize the individual's predisposition, for example, of developing one or more diseases, or to maintain good health. Many adults have one or more nutrient deficiencies, including vitamins and minerals. As diets vary from person to person and as most foods have hundreds of nutrients in minute amounts, the so-called "one-a-day" approach to nutritional supplements may not be appropriate for any given individual. Aspects of the present invention tailor nutritional supplements to the individual based at least in part on each individual's dietary intake, predisposition to particular diseases or health-related problems, lifestyle factors, etc.

Accordingly, various embodiments of the present invention may be directed toward manufacturing, providing, packaging and/or delivering customized nutraceuticals to an individual. A circular carousel (for example) may be used that holds containers to be filled. Based at least in part on the quantity and/or type of the nutraceutical(s) to be provided, a properly-sized container may be fed onto the carousel from a multi-channel feeding device. The location of the container on the carousel may be associated by a computer to a particular individual's order or requirements pursuant to the lifestyle and medical/diet information produced by the systems and methods in the present invention. In some instances, multiple containers may be designated for an individual order.

The carousel rotates through a series of stops. At each stop, a feeding device releases or withholds a supplement delivery unit (e.g., pill, capsule, etc.). The appropriate number of units would be inserted into the container. This continues until the entire range of stops is completed thereby filling the individual's order. Depending on the number of nutraceuticals offered, any number of additional carousels may be used as would be apparent.

Various embodiments of the invention may also provide individualized capsule/tablet formulations. In this regard, a carousel may rotate through a series of stops, where, at each stop, a particular herb, or supplement is added. Once mixed, the material would be transferred to an encapsulation-tablet pressing device that would inject the material into the proper sized capsule or compress the material into the proper sized tablet. All of the these operations (and the ones discussed above) may be controlled by one or more microprocessors, data storage devices, and sensors as would be apparent.

Individualized dietary supplement and nutraceutical formulations may provide individuals the precise combination of vitamins, minerals, herbs, antioxidants and nutraceuticals they actually need. Accordingly, each individual may be screened through a combination of methods that include gathering information regarding their normal eating habits and genetic makeup.

Medication/Supplement Tracking

FIG. 3 illustrates an embodiment of the present invention that includes a radio transmitter 100 the size of or made part of a pill or capsule. In some embodiments, the transmitter is made part of a pill which the individual is required to take (medication, supplement, and the like). When ingested, the pill travels to the individual's stomach 102, where stomach acid 104 "activates" the transmitter, which in turn sends a signal 106 to a 108 radio receiver. The receiver may be connected to the individual's computer 110, for example, and upon receiving the signal, in some embodiments, the receiver forwards another signal along communication line 109 to the computer 110 indicating that the individual has taken his medication. Thus, time and date information may be automatically logged and periodically uploaded to a central monitoring station 114 periodically. In some embodiments of the invention, the system perform real-time monitoring to verify whether an individual has taken a medication within a certain time.

Figure 4:
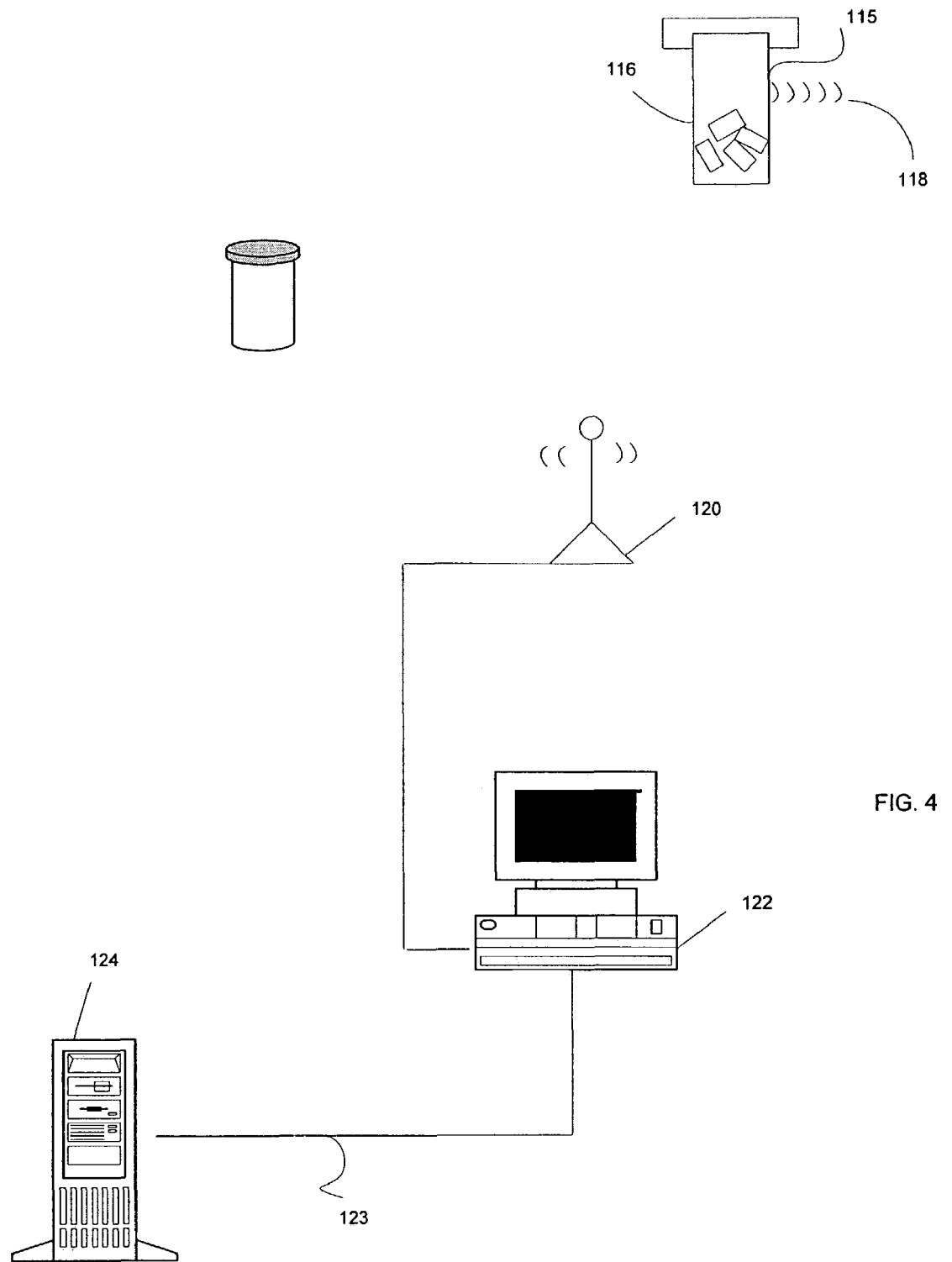
FIG. 4 illustrates an alternative tracking system according to another embodiment of the present invention.

FIG. 4 illustrates an embodiment of the invention that integrates or otherwise co-locates a sensor/transmitter 115 with a medication/supplement package. The act of opening the package 116, or dispensing a pill, for example, may initiate transmission of a radio signal 118 that is received by a radio receiver 120. The receiver, accordingly, may be connected to the individual's computer 122 so that the time at which the package was opened or the pill dispensed could be recorded and/or uploaded (via the internet 123, for example)

to a central monitoring station 124. The presumption is that opening the container indicates taking the medication as instructed. Other mechanisms using fewer or additional components to communicate and/or relay the signal from the transmitter to the central monitoring station 124 may be utilized as would be apparent.

In both cases, failure to receive affirmative information that the medication-related act is being taken would automatically trigger an intervention. The intervention may be live, as in, for example, an individual contacting the patient, or automated, as in for example, an email or voice message delivered to a phone, PDA, computer, etc.

Security/Privacy

In view of the enormous amount of confidential information of individual's stored and tracked by the systems and methods according to the present invention, an embodiment of the present invention utilizes security measures to prevent inadvertent or unauthorized release of potentially sensitive information. One such security measure includes the use of biometrics. Specifically, as illustrated in FIG. 5, at a workstation or other device that interacts with the systems and/or methods of the present invention, a keyboard 126 coupled to the workstation or other device used to access the system (keypad on a phone or cell phone, stylus or touch pad on a PDA, etc.) may include a micro-sensor 125. In embodiment employing a keyboard or keypad, micro-sensor 125 may be placed on one or more keys to determine and monitor the fingerprint(s) of the user of the keyboard. In some embodiments, the micro-fingerprint sensors are included on a home row 128 of a QWERTY keyboard 126, (i.e., the row including 'a,' 's,' 'd,' 'f,' 'j,' 'k,' 'l,' and ';' keys, as, for example, these keys are often used; although any number and/or combination of keys may be used as would be apparent. Micro-sensor 125 may be incorporated in other types of devices as would also be apparent. In these various embodiments of the invention, only users registered with the system may access a particular workstation or network, and continue to access the same once a session is initiated.

Some embodiments may include a warning that requires the user to take some affirmative action to authenticate himself within a predetermine time period. Such an action may include authentication through a standard pad attached to the keyboard, voice-print authentication, or any other method, within, for example, ten seconds.

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto. The contents of any references cited throughout this application are hereby incorporated by reference. The appropriate components, processes, and methods of those documents may be selected for the present invention and embodiments thereof.

What is claimed is:

1. A system for determining whether consumption of an item falls within a lifestyle for minimizing an individual's predisposition for developing a disease, the system comprising:

inputting means for inputting a code of a product for consumption by an individual into a wireless communication device;

first communicating means for communicating the code via the wireless communications device to a remote system;

receiving means for receiving the code by the remote system;

determining means for determining the product associated with the code;

querying means for querying a database to determine whether the product or a closely related product is contained therein, wherein said database comprises data domains comprising a scientific domain, genetic domain, and transactional domain, wherein the transactional domain comprises the code for the product;

analyzing means for interpreting the data in the data domains to determine whether the consumption of the product is related to minimizing a disease state; and second communicating means for communicating the analysis from the remote system to the wireless communication device.

2. A computer readable medium having computer instructions provided thereon for enabling a computer to perform a method for determining whether consumption of an item falls within a lifestyle for minimizing an individual's predisposition for developing a disease, the method comprising:

inputting a code of a product for consumption by an individual into a wireless communication device;

communicating the code via the wireless communications device to a remote system;

receiving the code by the remote system;

determining the product associated with the code;

querying means for querying a database to determine whether the product or a closely related product is contained therein, wherein said database comprises data domains comprising a scientific domain, genetic domain, and transactional domain, wherein the transactional domain comprises the code for the product;

analyzing means for interpreting the data in the data domains to determine whether the consumption of the product is related to minimizing a disease state; and communicating the analysis from the remote system to the wireless communication device.

3. An application program operational on a computer system for performing a method for determining whether consumption of an item falls within a lifestyle for minimizing an individual's predisposition for developing a disease, the method comprising:

inputting a code of a product for consumption by an individual into a wireless communication device;

communicating the code via the wireless communications device to a remote system;

receiving the code by the remote system;

determining the product associated with the code;

querying means for querying a database to determine whether the product or a closely related product is contained therein, wherein said database comprises data domains comprising a scientific domain, genetic domain, and transactional domain, wherein the transactional domain comprises the code for the product;

analyzing means for interpreting the data in the data domains to determine whether the consumption of the product is related to minimizing a disease state; and communicating the analysis from the remote system to the wireless communication device.

4. A method for determining whether consumption of an item falls within a lifestyle for minimizing an individual's predisposition for developing a disease, the method comprising: inputting a code of a product for consumption by an individual into a wireless communication device;
communicating the code via the wireless communications device to a remote system;
receiving the code by the remote system;
determining the product associated with the code;
determining the associated nutritional profile of the product; querying a database to determine whether the nutritional provide of the product fall within a lifestyle of the individual, wherein said database comprises data domains comprising a scientific domain, genetic domain, and transactional domain, wherein the transactional domain comprises the code for the product;
analyzing means for interpreting the data in the data domains to determine whether the consumption of the product is related to minimizing a disease state; and
communicating the analysis from the remote system to the wireless communication device.

5. The method according to claim 4, wherein inputting comprising scanning the product with a scanner in communication with the wireless communication device.

6. The method according to claim 4, wherein the wireless communication is selected from the group consisting of: cell phone, a pager, an email device, a radio, and a camera.

7. The method according to claim 4, wherein the wireless communications device includes a keypad for inputting alphanumerics.

8. The method according to claim 4, wherein the lifestyle database includes personalized data associated with the individual for at least one of dietary, nutritional, genetic, medical conditions, hereditary, behavior and habits of the individual.

9. The method according to claim 4, wherein inputting comprises speaking the code into the wireless communications device.

10. A computer readable medium having computer instructions provided thereon to enable a computer to perform a method for determining whether consumption of an item falls within a lifestyle for minimizing an individual's predisposition for developing a disease, the method comprising:
inputting a code of a product for consumption by an individual into a wireless communication device;
communicating the code via the wireless communications device to a remote system;
receiving the code by the remote system;
determining the product associated with the code;
determining the associated nutritional profile of the product;
querying a database to determine whether the nutritional provide of the product fall within a lifestyle of the individual, wherein said database comprises data domains comprising a scientific domain, genetic domain, and transactional domain, wherein the transactional domain comprises the code for the product;
analyzing means for interpreting the data in the data domains to determine whether the consumption of the product is related to minimizing a disease state; and
communicating the analysis from the remote system to the wireless communication device.

11. An application program operational on a computer system for performing a method for determining whether consumption of an item falls within a lifestyle for minimizing an individual's predisposition for developing a disease, the method comprising:
inputting a code of a product for consumption by an individual into a wireless communication device;
communicating the code via the wireless communications device to a remote system;
receiving the code by the remote system;
determining the product associated with the code;
determining the associated nutritional profile of the product;
querying a database to determine whether the nutritional provide of the product fall within a lifestyle of the individual, wherein said database comprises data domains comprising a scientific domain, genetic domain, and transactional domain, wherein the transactional domain comprises the code for the product;
analyzing means for interpreting the data in the data domains to determine whether the consumption of the product is related to minimizing a disease state; and
communicating the analysis from the remote system to the wireless communication device.

12. A system for determining whether consumption of an item falls within a lifestyle for minimizing an individual's predisposition for developing a disease, the system comprising: inputting means for inputting a code of a product for consumption by an individual into a wireless communication device;
first communicating means for communicating the code via the wireless communications device to a remote system;
receiving means for receiving the code by the remote system;
first determining means for determining the product associated with the code;
second determining the associated nutritional profile of the product;
querying means for querying a database to determine whether the nutritional provide of the product fall within a lifestyle of the individual, wherein said database comprises data domains comprising a scientific domain, genetic domain, and transactional domain, wherein the transactional domain comprises the code for the product; analyzing means for interpreting the data in the data domains to determine whether the consumption of the product is related to minimizing disease state; and
second communicating means for communicating the analysis from the remote system to the wireless communication device.

13. A method for determining whether an item falls within a lifestyle for minimizing an individual's predisposition for developing a disease, the method comprising:
providing an electronic identification on the lifestyle item;
communicating the electronic identification via a wireless communication device to a remote system;
determining the lifestyle item associated with the electronic information;
querying a database to determine whether the lifestyle item is associated with data contained therein, data domains comprising a scientific domain, genetic domain, and transactional domain, wherein the transactional domain comprises the code for the product;
analyzing means for interpreting the data in the data domains to determine whether the consumption of the product is related to minimizing a disease state;
forwarding the analysis from the remote system to the wireless communication device; and
presenting the analysis with the wireless communication device.

14. A system for determining whether an item falls within a lifestyle for minimizing an individual's predisposition for developing a disease, the system comprising:
an electronic identifier provided on the lifestyle item;

communicating means for communicating the information contained in the electronic identifier via a wireless communication device to a remote system;

determining means for determining the lifestyle item associated with the electronic information;

querying means for querying a database to determine whether the lifestyle item is associated with data contained therein, wherein said database comprises data domains comprising a scientific domain, genetic domain, and transactional domain, wherein the transactional domain comprises the code for the product;

analyzing means for interpreting the data in the data domains to determine whether the consumption of the product is related to minimizing a disease state;

forwarding means for forwarding the analysis from the remote system to the wireless communication device; and presenting means for presenting the analysis with the wireless communication device.

15. A computer readable medium having computer instructions provided thereon for enabling a computer to perform a method for determining whether an item falls within a lifestyle for minimizing an individual's predisposition for developing a disease, the method comprising: providing an electronic identification on the lifestyle item;

communicating the electronic identification via a wireless communication device to a remote system;

determining the lifestyle item associated with the electronic information;

querying a database to determine whether the lifestyle item is associated with data contained therein, data domains comprising a scientific domain, genetic domain, and transactional domain, wherein the transactional domain comprises the code for the product;

analyzing means for interpreting the data in the data domains to determine whether the consumption of the product is related to minimizing a disease state;

forwarding the analysis from the remote system to the wireless communication device;

and presenting the analysis with the wireless communication device.

16. An application program operational on a computer for performing a method for determining whether an item falls within a lifestyle for minimizing an individual's predisposition for developing a disease, the method comprising:

providing an electronic identification on the lifestyle item;

communicating the electronic identification via a wireless communication device to a remote system;

determining the lifestyle item associated with the electronic information;

querying a database to determine whether the lifestyle item is associated with data contained therein, data domains comprising a scientific domain, genetic domain, and transactional domain, wherein the transactional domain comprises the code for the product;

analyzing means for interpreting the data in the data domains to determine whether the consumption of the product is related to minimizing a disease state;

forwarding the analysis from the remote system to the wireless communication device;

and presenting the analysis with the wireless communication device.

17. A method for producing a customized supplement for an individual for minimizing an individual's predisposition for developing a disease and/or maintaining health, the method comprising:

providing personal information of an individual;

querying a database to determine a disease for which the individual has a predisposition for developing, data domains comprising a scientific domain, genetic domain, and transactional domain, wherein the transactional domain comprises the code for the product;

analyzing means for interpreting the data in the data domains to determine whether the consumption of the product is related to minimizing a disease state;

querying a supplement database to determine one or more dietary supplements to be ingested by the individual to minimize the individual's predisposition for developing the disease and/or maintaining health.

18. The method according to claim 17, further comprising packaging the supplements found in the query of the supplement database to produce a supplement package and delivering the supplement package to the individual.

19. A computer readable medium having computer instructions provided thereon for enabling a computer system to perform a method for producing a customized supplement for an individual for minimizing an individual's predisposition for developing a disease and/or maintaining health, the method comprising:

providing personal information of an individual;

querying a database to determine a disease for which the individual has a predisposition for developing, data domains comprising a scientific domain, genetic domain, and transactional domain, wherein the transactional domain comprises the code for the product;

analyzing means for interpreting the data in the data domains to determine whether the consumption of the product is related to minimizing a disease state;

querying a supplement database to determine one or more dietary supplements to be ingested by the individual to minimize the individual's predisposition for developing the disease and/or maintaining health.

20. The medium according to claim 19, wherein the method further comprising packaging the supplements found in the query of the supplement database to produce a supplement package and delivering the supplement package to the individual.

21. A computer application program operable on a computer system for enabling the computer system to perform a method for producing a customized supplement for an individual for minimizing an individual's predisposition for developing a disease and/or maintaining health, the method comprising:

providing personal information of an individual;

querying a database to determine a disease for which the individual has a predisposition for developing, data domains comprising a scientific domain, genetic domain, and transactional domain, wherein the transactional domain comprises the code for the product;

analyzing means for interpreting the data in the data domains to determine whether the consumption of the product is related to minimizing a disease state;

querying a supplement database to determine one or more dietary supplements to be ingested by the individual to minimize the individual's predisposition for developing the disease and/or maintaining health.

22. The computer application program according to claim 21, wherein the method further comprising packaging the supplements found in the query of the supplement database to produce a supplement package and delivering the supplement package to the individual.

* * * * *